(12) United States Patent
Akutsu

(10) Patent No.: US 9,731,041 B2
(45) Date of Patent: Aug. 15, 2017

(54) METHOD AND APPARATUS FOR STERILIZATION WITH NITROGEN OXIDE

(71) Applicant: ENA Co., Ltd., Tokyo (JP)

(72) Inventor: Toshin Akutsu, Tokyo (JP)

(73) Assignee: ENA Co., Ltd., Tokyo (JP)

( * ) Notice: Subject to any disclaimer, the term of this patent is extended or adjusted under 35 U.S.C. 154(b) by 0 days.

(21) Appl. No.: 14/375,046

(22) PCT Filed: Apr. 19, 2013

(86) PCT No.: PCT/JP2013/002662
§ 371 (c)(1),
(2) Date: Jul. 28, 2014

(87) PCT Pub. No.: WO2013/157276
PCT Pub. Date: Oct. 24, 2013

(65) Prior Publication Data
US 2015/0037206 A1    Feb. 5, 2015

(30) Foreign Application Priority Data

Apr. 19, 2012 (JP) .................. 2012-095284
Apr. 19, 2012 (JP) .................. 2012-095285

(51) Int. Cl.
*A61L 2/20* (2006.01)
*A61L 2/18* (2006.01)
(Continued)

(52) U.S. Cl.
CPC .............. *A61L 2/20* (2013.01); *A23L 3/3409* (2013.01); *A23L 3/3445* (2013.01); *A61L 2/22* (2013.01);
(Continued)

(58) Field of Classification Search
CPC ...................................... A23L 3/3409
See application file for complete search history.

(56) References Cited

U.S. PATENT DOCUMENTS 4,238,447 A * 12/1980 Wolff ............................. 422/26
4,552,728 A * 11/1985 Taylor ......................... 422/300
(Continued)

FOREIGN PATENT DOCUMENTS

GB      2384185 B     12/2003
JP      6111050 A      1/1986
(Continued)

OTHER PUBLICATIONS

Muller, Fundamentals of Thermodynamics and Applications, 2009, Springer-Verlag Berlin Heidelberg, p. 70-71.*
(Continued)

*Primary Examiner* — Kevin Joyner
*Assistant Examiner* — Holly Mull
(74) *Attorney, Agent, or Firm* — Bachman & LaPointe, PC

(57) ABSTRACT

Nitrogen oxide is used to safely sterilize inside of a space area or an object arranged within the space area. A sterilization method is provided to comprise: introducing nitrogen oxide liquid stored in a vessel (4) into a space area (2, 2', 2") to gasify nitrogen oxide liquid, and sterilizing inside of space area (2, 2', 2") or object (1) arranged in space area (2, 2', 2") with nitrogen oxide gas evaporated from nitrogen oxide liquid to completely annihilate and destroy microorganisms inclusive of bacteria and virus with nitrogen oxide gas for preventing the infection by microorganisms to human body and damage to precision components.

8 Claims, 9 Drawing Sheets

(51) Int. Cl.
| | |
|---|---|
| *C01B 21/36* | (2006.01) |
| *A23L 3/3409* | (2006.01) |
| *A61L 2/22* | (2006.01) |
| *A23L 3/3445* | (2006.01) |
| *A61L 9/04* | (2006.01) |
| *A61L 9/14* | (2006.01) |

(52) U.S. Cl.
CPC .............. *A61L 9/046* (2013.01); *A61L 9/14* (2013.01); *C01B 21/36* (2013.01); *A61L 2202/24* (2013.01)

(56) References Cited

U.S. PATENT DOCUMENTS

| | | | |
|---|---|---|---|
| 5,122,344 A | 6/1992 | Schmoegner | |
| 5,348,711 A * | 9/1994 | Johnson et al. | 422/300 |
| 5,676,531 A * | 10/1997 | Muscarella et al. | 417/413.1 |
| 5,750,072 A * | 5/1998 | Sangster et al. | 422/22 |
| 6,451,254 B1 * | 9/2002 | Wang et al. | 422/33 |
| 6,610,251 B1 * | 8/2003 | Kanno | 422/39 |
| 7,357,296 B2 * | 4/2008 | Stemmle | 232/17 |
| 8,017,074 B2 | 9/2011 | Arnold et al. | |
| 8,425,837 B2 | 4/2013 | Carbone et al. | |
| 8,721,984 B2 | 5/2014 | Carbone et al. | |
| 8,747,739 B2 | 6/2014 | Parker et al. | |
| 2004/0013777 A1 | 1/2004 | Hallstadius | |
| 2007/0014686 A1 | 1/2007 | Arnold et al. | |
| 2009/0123333 A1 | 5/2009 | Parker et al. | |
| 2011/0085938 A1 | 4/2011 | Carbone et al. | |
| 2011/0318225 A1 | 12/2011 | Arnold et al. | |
| 2013/0230430 A1 | 9/2013 | Carbone et al. | |

FOREIGN PATENT DOCUMENTS

| | | |
|---|---|---|
| JP | 4503026 A | 6/1992 |
| JP | 1147242 A | 2/1999 |
| JP | 2001-29440 A | 2/2001 |
| JP | 2001340432 A | 12/2001 |
| JP | 2003535327 A | 11/2003 |
| JP | 2006-81802 A | 3/2006 |
| JP | 2006068122 A | 3/2006 |
| JP | 2009513213 A | 4/2009 |
| JP | 2009542333 A | 12/2009 |
| JP | 2011004802 A | 1/2011 |
| JP | 2011050602 A | 3/2011 |
| WO | 9107193 A1 | 5/1991 |
| WO | 0192854 A1 | 12/2001 |
| WO | 2007049076 A1 | 5/2007 |
| WO | 2008005313 A2 | 1/2008 |
| WO | 2010096766 A1 | 8/2010 |
| WO | 2011/002700 A2 | 1/2011 |

OTHER PUBLICATIONS

Japanese Office action for Japanese Application No. 2013-088415 dated Nov. 25, 2014.
Supplementary European Search Report for EP 13778168.8, dated Apr. 16, 2015.
Japanese Office action for Japanese Application No. 2014-86406 dated Dec. 15, 2015.
Chinese Office action for Chinese Application No. 201380020461.9 dated Jan. 28, 2016.
Physical Chemistry, pp. 277-285, vol. 1, Published Jul. 31, 2005.

* cited by examiner

METHOD AND APPARATUS FOR STERILIZATION WITH NITROGEN OXIDE

TECHNICAL FIELD

This invention relates to a method and an apparatus for sterilization with nitrogen oxide to sterilize microbially-contaminated objects. It also relates to a method and an apparatus for sterilization with nitrogen oxide to disinfect inside of a space area or microbially-contaminated objects disposed within the space area.

BACKGROUND OF THE INVENTION

Medical and health-care fields, research and development sectors typically use autoclaves or steam sterilizers to sterilize microbially-contaminated medical instruments or test devices for their reuse. The autoclave is used for a sterilization technology that comprises for example, putting dirty medical instruments in a compression chamber, keeping for several tens of minutes the instruments within the chamber of a pressurized, heated and humid atmosphere, and hydrolyzing and decomposing microorganism biopolymer into their extinction at a high temperature to annihilate all bacteria and viruses. One such sterilizing process with autoclave, however, is defective because it disadvantageously requires heating an inside of autoclave vessel up to a temperature of 130 degrees C. that is not applicable to sterilization of low heat-resistant instruments for example made of rubber. This process also raises a further problem with sterilization of plastic instruments because they are subject to heating cycles that cause plastic instruments to repetitively, physically and thermally expand and contract. This allows pressurized water vapor to penetrate into interstices inherently formed on plastics under pressure of approximately 2 atmospheres while facilitating deterioration of plastics.

An alternative sterilizing technology with gas of ethylene oxide ($C_2H_4O$) (EOG) can be applied to disinfection of lower heat- and moisture-resistant rubbers and plastics because the technology can work at a lower temperature, at a lower pressure and at a lower humidity than those in autoclave. However, it must utilize highly reactive ethylene oxide gas that disadvantageously brings dangers for people because of its ignitability and explodability under pressure. Also, it is very troublesome to handle and has high toxicity to human body. Human inhalation of ethylene oxide gas may cause a variety of symptoms for example membrane irritation of upper airway, vomiting and headache, and it may be a carcinogen damaging zoetic deoxyribonucleic acid. The United States Pharmacopeia (USP) has strengthened the regulation for usage of ethylene oxide gas that thereby increases needs of better alternative.

Now, one of high-profile sterilants is nitrogen oxide that is relatively easy to handle for sterilization with neither application of heat and pressure to the sterilant. Nitrogen oxide is a generic or collective name of nitrogen-oxygen compound groups consisting of nitric monoxide (NO), nitrogen dioxide ($NO_2$), nitrous oxide (dinitrogen oxide) ($N_2O$), dinitrogen trioxide ($N_2O_3$), dinitrogen tetraoxide ($N_2O_4$) and dinitrogen pentoxide ($N_2O_5$). Patent Document 1 below listed discloses a system for sterilizing and decontamianting a contaminated object, i.e. a dirty medical device by exposing it to one or more nitrogen oxide sterilizing gases selected from groups of NO, $NO_2$, $NO_3$, $N_2O_3$, $N_2O_4$, $N_2O_5$, $N_2O$ and their mixture. The system stores sterilant feedstock that is turned into nitrogen oxide gas to thereby sterilize the object within a hermetically sealed chamber.

Patent Document 2 mentioned below discloses a sterilization apparatus that comprises: a sterile chamber to define a hermetically closed space, contaminated objects arranged within the sterile chamber, the objects including medical instruments such as scalpel, forceps, catheter and food packaging materials such as packaging sheets, trays, bottles and a plasma generator for producing nitrogen oxide gas at an atmospheric pressure to introduce the gas from plasma generator through catalysts into the sterile chamber and to expose the dirty objects to nitrogen oxide gas for their sterilization. The plasma generator comprises a microwave generator and a plasma activation nozzle for receiving microwave energy from the microwave generator to convert feedstock gas into plasma. Thus, Patent Document 2 shows production of nitrogen oxide plasma derived from nitrogen and oxygen in feedstock gas.

Patent document 1 shows usage of a reaction chamber to generate nitrogen oxide gas by reaction of oxalic acid and diazeniumdiolate compound $[R_3—C(R_1)_x(N_2O_2R_2)_y]$ as a feedstock coming into sterilant gas or by reaction of acid and another type of sterilant-gas occurring feedstock. However, these reactions are disadvantageous because they require proper and strict controls of the reaction conditions in reaction chamber when mixing a plurality of materials within reaction chamber to turn them into nitrogen oxide gas to be sent to a sterilization chamber, and failure of proper controls for the reactive conditions would lead to unstable concentration in generated nitrogen oxide that would result in insufficient disinfection of an object in sterilization chamber. In another aspect, with excessive amount of nitrogen oxide fed into sterilization chamber, that would cause unfavorable adherence of nitrogen oxide on sterilized medical instruments at a high concentration against their subsequent safe usage. Also, in fact, actual medical practices would find difficulty in applying sterilization to medical instruments if each sterilization requires mixing of solid feedstock and acid. In addition, acids are dangerous when handling for transportation and storage.

Patent Document 2 discloses a sterilization apparatus for generating nitrogen oxide gas through plasma gasification that utilizes nitrogen and oxygen in the air as raw materials, however, it has a very low efficiency in generation of nitrogen oxide gas although not involving any risk in conveying and storing the raw materials. For that reason, the sterilization apparatus of Patent Document 2 is defective because it must spend so much time and high energy cost not only in preparation for generating and filling nitrogen oxide gas inside of sterilization chamber prior to the start of sterilization but also in completed sterilization of the object while keeping a predetermined concentration of nitrogen oxide within sterilization chamber. In addition, the apparatus in Patent Document 2 must generate nitrogen oxide in a plasma gasifier and further undesirably convert it into highly sterilizing nitrogen dioxide by means of expensive catalyst such as platinum or palladium that may raise the production cost.

Moreover, previous studies and researches including Patent Documents 1 and 2 have never proposed any recovery method for efficiently and completely collecting a sterilant from a sterilization chamber after sterilization. Therefore, prior art sterilizations are dangerous because they cannot completely remove poisonous sterilant at a specific density range particularly around specific configurations of medical instruments to be safely reused or recycled after sterilization.

Sterilization chambers such as clean rooms, clean booths or isolators are kept in an almost aseptic condition, preventing intrusion of bacteria, microorganism and dust into the chamber for pharmaceutical research, manufacture and inspection. Concentration of airborne particles is controlled within clean rooms with their inner volume of approximately 20 to 300 $m^3$ wherein inflow, generation and stagnation of microparticles are controlled to their minimum while also controlling temperature, humidity and pressure of clean rooms as necessary. Clean booths have been developed to clean and sterilize a small working space to define a simplified clean room of its inner volume approximately 2 to 30 $m^3$. Isolators form a large chamber of its inner volume of approximately 2 to 20 $m^3$ isolated from the atmosphere to conduct inner operations within the chamber through external manual manipulations with rubber gloves provided before a transparent front wall of each isolator.

Air within each clean room is vacuumed up or circulated by an air blower to remove airborne microparticles through filters and thereby keep clean rooms in the almost sterile condition. In this way, removal of airborne microparticles basically allows for exclusion of microorganisms and bacteria to thereby prevent microbial contamination in clean room. However, in fact, such filtering microparticles alone fails to fully eliminate bacteria because it cannot completely remove bacteria in the stagnant air around corners of clean rooms. Taking in air and blowing air through filters cannot fully remove contaminants such as microorganisms adhering or attaching onto wall and floor surfaces in clean room. Thus, such air filtering methods require periodical sterilization of inside in clean rooms.

A gas sterilization is known for disinfecting treatment of unsterilized objects such as inside of clean rooms utilizing a formaldehyde, hydrogen peroxide ($H_2O_2$) or ozone ($O_3$) gas sterilizer. One such gas sterilizer is used to first feed a sterilizing gas from a gas generator or gas tank into a sterilization chamber to repletion, and then to keep the chamber in the gas repletion condition for a certain period of time to annihilate microorganisms and bacteria floating in the air or adhering on sterilization chamber walls.

The gas sterilization can also be applied to sterilization of microbially contaminated medical devices for their recycle. Sterilization of medical instruments typically utilizes autoclaves (or high-pressure steam sterilizers), however, they are defective because they disadvantageously require heating inside of an autoclave vessel up to a temperature of 130 degrees C., and so autoclaves cannot be applied to low heat-resistant instruments for example made of rubber because they must use pressurized water vapor that penetrates into interstices inherently formed on plastics under the pressure of approximately 2 atmospheres while facilitating deterioration of plastics. Accordingly, rather gas sterilization is advantageous to disinfection of heat- and pressure-irresistible medical instruments.

Gas sterilization of medical instruments often uses ethylene oxide gas (EOG). Ethylene oxide is a transparent, colorless and ether-smelling substance of the evaporation temperature at approximately 20 degrees C. Ethylene oxide gas for sterilization is diluted with carbon dioxide gas to prepare a mixed gas filled in a high-pressure vessel that consists of approximately 20% ethylene oxide and approximately 80% carbon dioxide gas. The mixed gas with ethylene oxide is supplied from high-pressure vessel into a clean room or into a spatial area of a sterilization chamber kept at a predetermined ethylene oxide gas concentration where medical instruments are disposed for a certain period of time for their sterilization.

Patent Document 3 discloses a sterilization system for disinfecting an isolator with hydrogen peroxide for asepsis of a spatial area. The system comprises a sterilizing gas source, an isolator and gas conduits for connecting the gas source and isolator, wherein the gas source has an evaporator to vaporize hydrogen peroxide, an ejector for dropping hydrogen peroxide liquid in the evaporator, and a heater for heating air sent to the evaporator to sterilize inside of the isolator with hydrogen peroxide gas.

Patent Document 2 below discloses an apparatus for antisepticizing unsterilized objects (such as medical instruments or containers in use for medical purpose) by an ozone sterilizer in a sterile area. In this case, the objects in sterile area are exposed to ozone gas for a certain period of time, and then, air is introduced into sterile area through an aeration line connected thereto to discharge ozone gas.

Ethylene oxide gas has the high toxicity to human body that may cause irritation on upper airway membranes, vomiting and headache, and that may be a carcinogen damaging deoxyribonucleic acid (DNA). Thus, it would be too dangerous for human health to inhale remaining ethylene oxide gas after sterilization.

Patent Document 3 shows an isolator system that requires a lot of energy for a heater to heat and vaporize hydrogen peroxide of the boiling point 141 degrees C., and the isolator is further defective because hydrogen peroxide steam of a very high temperature may denature and deteriorate heat-labile materials (rubber or resin) in the isolator. Also, the isolator system in Patent Document 3 fails to precisely control a supply amount of hydrogen peroxide, and the excessive supply amount may lead to a corrosion to metallic components in isolator and a residue of hydrogen peroxide after sterilization, and the insufficient supply amount may fail to completely destroy microorganisms and bacteria in isolator. In general, hydrogen peroxide is highly reactive and intensely degradable at a room temperature and may ignite and explode with self-decomposition particularly at a high concentration. Attachment of hydrogen peroxide to a human skin will develop painful vitiligo on the skin, and therefore, it is very troublesome to handle the substance for transportation and storage. Hydrogen peroxide is also highly corrosive to metallic materials.

Patent Document 4 teaches an ozone sterilizer that controls interior pressure in a sterile area to a negative level below normal pressure to then supply ozone into the sterile area. This ozone sterilizer is disadvantageous because it generates ozone from air source with its too low efficiency and takes a long time to replete ozone of a predetermined concentration in the sterile area of large volume, and it fails to precisely control the generated amount of ozone for exact adjustment of ozone concentration in the sterile area. The ozone sterilizer requires an ozone generator that generates ozone at the site of sterilization immediately before its usage because ozone is so chemically-unstable as to inherently and gradually proceed with the decomposition at a room temperature. For that reason, the ozone sterilizer must be made into a larger size of the whole sterilizing system that increases equipment installation and running costs inclusive of operating electricity costs. Also, ozone is too dangerous because of its strong oxidizability to deadly poison at high concentration, and human inhalation of ozone causes his or her viscera to be oxidized to erosion.

When nitrogen oxide is used as a sterilant in Patent Document 1, it must mix different kinds of materials within a reaction chamber to generate and supply a nitrogen oxide gas into spatial area while it is impossible to detect and control a precise yield of nitrogen oxide gas and also to be unable to feed nitrogen oxide gas at a predetermined precise concentration into the spatial area against full sterilization of medical devices therein. Adversely, excessive amount of nitrogen oxide into the chamber, would cause nitrogen oxide at the elevated concentration to unfavorably remain around and adhere on the sterilized objects to commit a safety violation. Also, if every sterilization requires the mixing procedure of solid sterile feedstock and acid, in fact it would be very difficult to be adopted in medical practice for sterilization of clean rooms and medical instruments. In addition, acids involve much danger in its usage and handling for transportation and storage.

[Patent Document 1] Japanese Patent Disclosure No. 2009-542333
[Patent Document 2] Japanese Patent Disclosure No. 2011-4802
[Patent Document 3] Japanese Patent Disclosure No. 2006-68122
[Patent Document 4] Japanese Patent Disclosure No. 2001-340432

Problem to be Solved by the Invention

Accordingly, a first object of the present invention is to provide a method and an apparatus for safely sterilizing microbially-contaminated objects with nitrogen oxide. A second object of the present invention is to provide a method and an apparatus for rapidly and certainly sterilizing any configuration of bug-polluted objects. A third object of the present invention is to provide a method and an apparatus for effectively recovering a sterilant used for sterilization without any remaining harmful sterilant on sterile objects.

A fourth object of the present invention is to provide an apparatus and a method for safely sterilizing airborne microorganisms and nonsterile objects within a space area typically at an atmospheric pressure. A fifth object of the present invention is to provide a safely- and easily-handled apparatus and method for sterilization by means of nitrogen oxide liquid as a sterilant feedstock. A sixth object of the present invention is to provide an apparatus and a method for rapidly generating a sterilant at a predetermined concentration to reliably sterilize microorganisms and unsterilized objects within a space area. A seventh object of the present invention is to provide a compact and inexpensive apparatus and its working method for sterilization without need of any large-sized sterilant generator.

SUMMARY OF THE INVENTION

A sterilization method according to the present invention comprises the steps of: arranging an object (1) within a space area (2), operating a decompressor (3) to reduce a pressure within the hermetically sealed space area (2), introducing a nitrogen oxide liquid retained in a vessel (4) into the space area (2) kept under the decompressed or vacuum condition to gasify the nitrogen oxide liquid within the space area (2), and sterilizing the object (1) in the space area (2) with the nitrogen oxide gas.

Nitrogen oxide liquid is introduced from vessel (4) into space area (2) that is decompressed or vacuumized below the saturated vapor pressure of nitrogen oxide to allow at least some of nitrogen oxide liquid to vaporize in the space area (2). Oxidative nitrogen oxide gas immediately spreads in the space area (2) to diffuse toward the whole of objects (1) within the space area (2) and to thereby rapidly and completely sterilize all the surfaces of intricately-shaped objects (1). The term "sterilization" herein means an aseptic condition of all proliferative microorganisms (mainly bacteria) being completely removed and destroyed or a condition of the possibility of microorganism growth being infinitely close to zero, i.e. the condition of the sterility assurance level (SAL) less than $10^{-6}$ in the existing probability of microorganisms after sterilization. Accordingly, to be exact, the sterilization is different from a word "disinfection" that reduces the ability of pathogenic microorganism but not annihilating all microorganisms, and also from another word "killing microorganisms" that is indifferent about killed target and killing level. The "sterilization" must completely inactivate the microorganism function in molecular biology or biotechnology. Also, the present invention can perform a depyrogenation process superior to sterilization by effectively removing also endotoxin that is bacterial dead bodies.

The present invention is advantageous because it may also introduce nitrogen oxide liquid into space area (2) to gasify it under a reduced pressure for sterilization at a predetermined stable concentration of nitrogen oxide, without mixing need of several materials and also without utilization of an expensive plasma generator or catalytic metals. Also, the invention may conveniently utilize a normal temperature and a normal pressure where preserving and treating nitrogen oxide liquid that inherently exists approximately at a normal temperature and a normal pressure, and therefore, it dispenses with an expensive high-pressure vessel for nitrogen oxide liquid, and it is easy to handle while significantly cutting down delivery and maintenance costs.

The sterilization method according to the present invention comprises the steps of: connecting a metering pump (34, 34') to a vessel (4) for storing nitrogen oxide liquid, operating metering pump (34, 34') to suck and supply the predetermined amount of nitrogen oxide liquid from vessel (4) toward a space area (2', 2") that is kept at the substantially atmospheric pressure, and injecting through a spray device (32) the predetermined amount of nitrogen oxide liquid into gas in space area (2', 2").

The sterilization apparatus according to the present invention, comprises: a vessel (4) for storing nitrogen oxide liquid, a hermetically sealed space area (2) in which an object (1) is arranged, space area (2) being connected to vessel (4), and a decompressor (3) for depressurizing space area (2). The sterilization apparatus can introduce nitrogen oxide liquid from vessel (4) into space area (2) under the decompressed or vacuum condition that allows nitrogen oxide liquid to gasify to effectively sterilize the object (1) in space area (2), and such a sterilization apparatus is easy to manufacture.

In another embodiment, the sterilization apparatus according to the present invention, comprises: a space area (2', 2") retained at a substantially atmospheric pressure, a hermetically sealable vessel (4) for storing nitrogen oxide liquid, and a spray device (32) for injecting, spraying or atomizing under pressure a predetermined amount of nitrogen oxide liquid fed from vessel (4) into a gas in space area (2', 2"). Metering pump (34, 34') is used to supply a predetermined amount of highly oxidative nitrogen oxide liquid from vessel (4) toward spray device (32) that sprays and immediately turns nitrogen oxide liquid into gas in space area (2', 2") at a substantially atmospheric pressure. Generated nitrogen oxide gas spreads and diffuses around the whole space area (2') for example inside of a clean room to keep the room at a predetermined concentration of nitrogen oxide gas to rapidly and effectively sterilize throughout space area (2'). Also, nitrogen oxide gas contacts and touches entire surfaces of unsterilized objects (1) for sterilization of the objects such as medical instruments (1) disposed in space area (2") of a sterilization chamber (60).

The term "sterilization" herein means the processing for completely annihilating all kinds of proliferative microorganisms (mainly bacteria) or for converging the microorganism growth possibility on zero, i.e. for reducing the sterility assurance level (SAL) less than $10^{-6}$ in the existing probability of microorganisms after sterilization, and the molecular biology or biotechnology requires to completely inactivate microorganism function for "sterilization". Accordingly, to be accurate, the sterilization is different from a word "disinfection" that only reduces ability of pathogenic microorganism without a purpose of annihilating all microorganisms, and it also different from another word "killing microorganisms" that is unrelated to killed targets and killing level. The present invention also contemplates a more advanced depyrogenation process for effectively removing endotoxin in bacterial dead bodies than sterilization.

Also, nitrogen oxide liquid can be held in a vessel (4) at a normal temperature under a minimum pressure to safely and easily charge and discharge the liquid into and from vessel (4) without need of any high-pressure tank. This easy handling allows for considerable cost reduction in delivery and maintenance of nitrogen oxide liquid relative to nitrogen oxide gas, and it also allows for a compact and inexpensive sterilization apparatus.

Effect of Invention

The present invention can use nitrogen oxide to completely annihilate and destroy microorganisms inclusive of bacteria and viruses attaching to unsterilized objects for prevention of infection to human body and damage to precision articles or instruments by microorganisms. Also, nitrogen oxide can be efficiently and safely introduced into a space area at a minimum pressure without any mixing operation of several substances to fill the space area with nitrogen oxide of a predetermined concentration with the shortened operation time and lowered energy cost for sterilization. In addition, after sterilization, used nitrogen oxide can be effectively and advantageously removed from sterilized objects without residual nitrogen oxide on the objects for their safe reuse.

Both of the sterilization method and apparatus according to the present invention utilize a technology for introducing nitrogen oxide into the sterilization chamber to completely annihilate and destroy microorganisms including bacteria and viruses airborne and attaching to unsterilized objects (for example medical instruments) in the space area for prevention of infection to human body and damage to precision articles by microorganisms. Also, relatively-safe nitrogen oxide liquid can be exactly measured to efficiently and safely introduce it into a space area approximately at an atmospheric pressure and turn it into nitrogen oxide gas without any mixing of several substances so that the space area has a predetermined stable concentration of nitrogen oxide gas with the shortened operation time and lowered energy cost for sterilization. Also, as the instant invention dispenses with a sterilant generator such as an ozonizer and a plasma generator, the whole invention's apparatus can be made into a small size with reduced initial and running costs.

EXPLANATION OF SYMBOLS (1) . . . an object (an object to be sterilized, a medical instrument), (2, 2', 2") . . . a space area (a cavity, an unsterilized space), (3) . . . a decompressor (a vacuum pump), (4) . . . a vessel, (6) . . . an outlet, (7) . . . a pressure controller (a recovery pressure valve), (25, 32) . . . a spray device (an ejector), (32a) . . . a jet orifice, (34, 34') . . . a metering pump, (34a) . . . a variable volume, (35) . . . a valve device (a three-way valve), (36) . . . a heater, (36a) . . . conduits, (37) . . . an outlet port, (47a) . . . a valve device (a suction valve), (47b) . . . a valve device (a delivery valve),

BEST MODE FOR CARRYING OUT THE INVENTION

In connection with FIGS. 1 to 5 of the drawings, embodiments of the present invention will be described hereinafter about the sterilization method and apparatus by nitrogen oxide.

Figure 1:
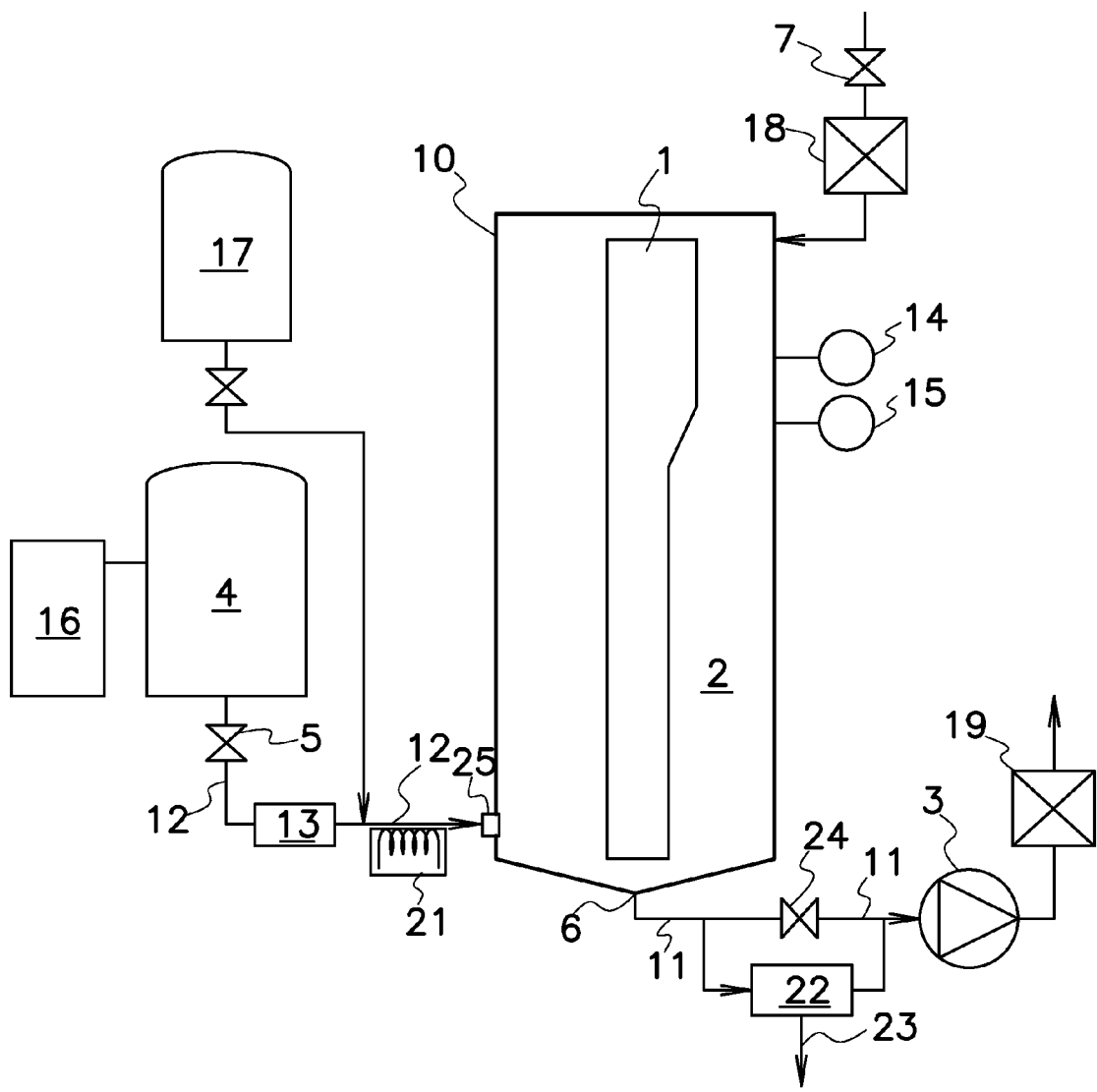
FIG. 1 A schematic diagram showing a first embodiment of the sterilization apparatus according to the present invention.

As shown in FIG. 1, a medical instrument 1 as an unsterilized object is arranged in a space area or a cavity 2 defined in a sterilization chamber 10. The present invention is applicable to medical instruments 1 made of any metallic, plastic and rubber materials resistible against deterioration by nitrogen oxide. Such medical instruments 1 may include surgical instruments such as scalpels, forceps, scissors and tweezers; diagnostic instruments such as flexible or rigid endoscopes, clinical thermometers, stethoscopes, funduscopes and aural speculums; therapeutic instruments such as catheters, injection syringes and medical tubing; and implantable medical instruments such as pacemakers, implantable aggregate and surgical pins. Objects 1 subject to sterilization may include medical containers such as plastic and glass containers, vials, spray cans, aluminum tubes, rubber plugs, elastomeric products and injection needles. The present invention is also applicable to preliminary, last-minute or emergent sterilization before use of medical instruments 1. A cavity 2 containing medical instruments 1 is covered with a door not shown, and is hermetically closed to keep a sealing condition of cavity 2.

Figure 2:
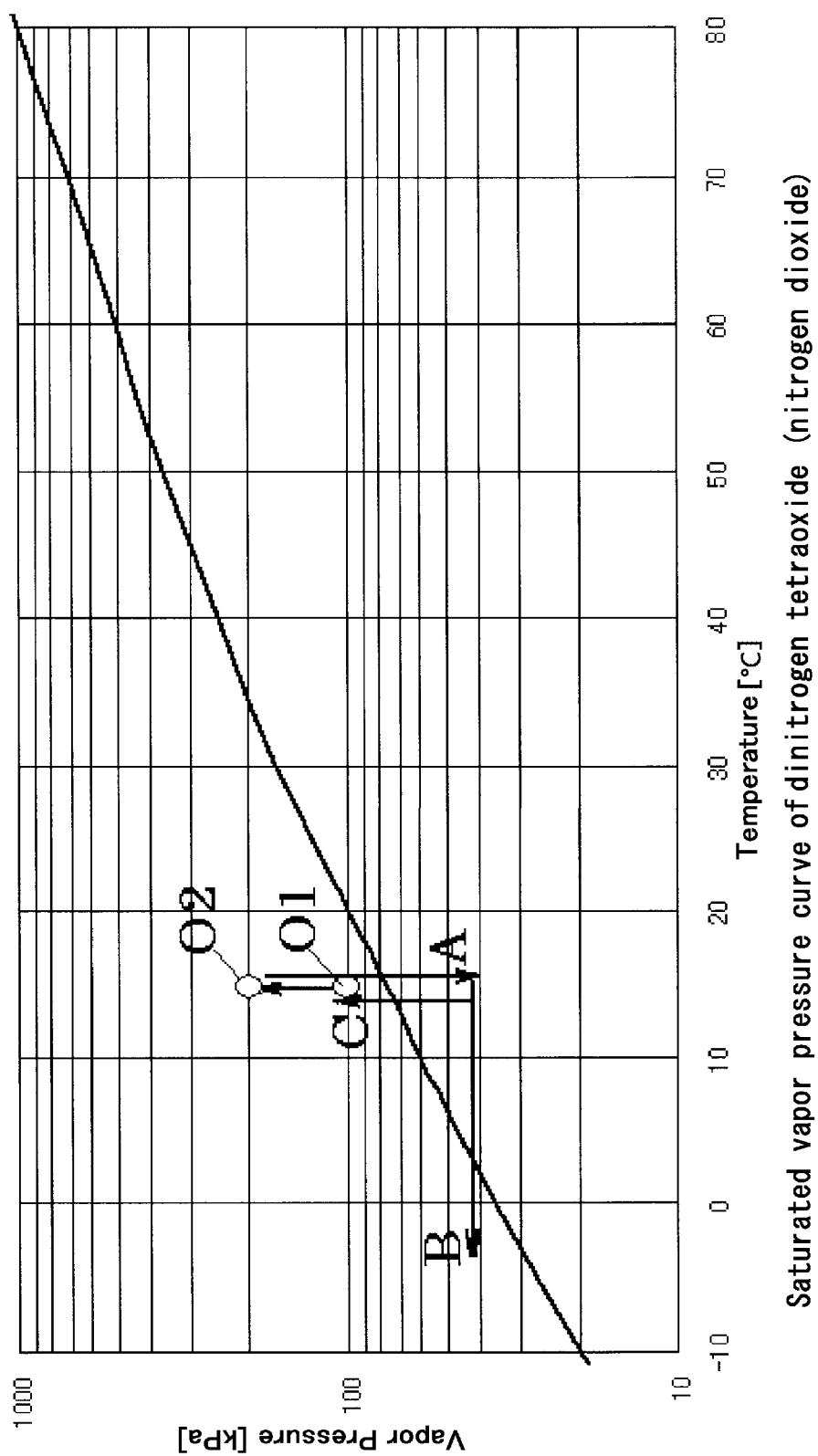
FIG. 2 A graph showing a saturated vapor pressure curve of dinitrogen tetraoxide (nitrogen dioxide) with vapor pressure variation over temperature variation.

A sterilization chamber 10 comprises a cavity 2 for accommodating medical instruments 1, an outlet 6 formed at the bottom of sterilization chamber 10, a suction pipe 11 connected to outlet 6, a vacuum pump (a decompressor) 3 connected to sterilization chamber 10 through outlet 6 and suction pipe 11, and a depressure valve 24 provided in suction pipe 11 wherein pressure within cavity 2 is reduced by exhausting gas with operation of vacuum pump 3 through opened valve 24. Vacuum pump 3 is connected to a removal filter 19 that may preferably remove bacteria from tainted gas discharged to the atmosphere through filter 19. Vessel 4 stores dinitrogen tetraoxide $N_2O_4$ and has an outlet at the bottom connected to a feed pipe 12 through a control valve 5 toward cavity 2 in sterilization chamber 10. Dinitrogen tetraoxide liquid of strongly oxidizing ability can be safely preserved in vessel 4 when it is filled with the liquid at a temperature less than 21 degrees C. (the boiling point) or at an absolute pressure of 200 kPa (approximately 2 atm). FIG. 2 shows a saturated vapor pressure curve of dinitrogen tetraoxide (nitrogen dioxide) indicating the chemical equilibrium profile between temperature variation [° C.] along the horizontal axis and vapor pressure variation [kPa] along the vertical axis wherein upper and lower sides of the curve respectively represent liquid and gas phases or states of dinitrogen tetraoxide. In this case, a point O1 indicates dinitrogen tetraoxide liquid at a temperature of 15 degrees C. and at an absolute pressure of 100 kPa, that is then moved to a point O2 by applying pressure to an absolute pressure of 200 kPa (approximately 2 atm) to fill the liquid in vessel 4. To this end, a compressor 16 is operated to allow nitrogen gas in compressor 16 to apply pressure on dinitrogen tetraoxide filled in vessel 4. The following chemical equilibrium equation is given between dinitrogen tetraoxide and nitrogen dioxide $NO_2$.

$$N_2O_4 = 2NO_2 - 57.2kJ$$

The chemical equilibrium equation indicates that the elevation of the pressure level at an unchanged temperature increases in existing proportion of dinitrogen tetraoxide so that the reaction goes to the left side in the equation. Adversely, the reduction in pressure level at a constant temperature leads to the increase in existing proportion of nitrogen dioxide so that the reaction goes to the right side in the equation. Colorless dinitrogen tetraoxide turns into reddish brown or yellow derived from gas or liquid of nitrogen dioxide through the chemical equilibrium state. Other than dinitrogen tetraoxide, the present invention contemplates nitrogen oxide liquid that may include dinitrogen trioxide and pentoxide, and combination of two or more of dinitrogen tetraoxide, trioxide and pentoxide.

To sterilize inside of cavity 2, vacuum pump 3 is operated to discharge air in cavity 2 outside with control valve 5 released so that dinitrogen tetraoxide under pressure in vessel 4 is fed through feed pipe 12 into cavity 2 kept in decompressed or vacuum condition. The apparatus of the invention is advantageous because it can deliver an exact amount of dinitrogen tetraoxide liquid toward cavity 2 while preventing dinitrogen tetraoxide liquid from gasifying on the way between vessel 4 and inlet of cavity 2 so that cavity 2 can always have a desirable and predetermined concentration of dinitrogen tetraoxide for reliable sterilization. A spray device or an ejector 25 is provided at an inlet of cavity 2 to atomize dinitrogen tetraoxide into gas. Spray device 25 may be a nozzle or valve. It is also possible to use spray device 25 with adjustable or fixed ejection area. A flowmeter 13 in feed pipe 12 measures flow rate of dinitrogen tetraoxide supplied toward cavity 2. Alternatively, flow rate of dinitrogen tetraoxide through control valve 5 may also be worked out based on a pressure difference between vessel 4 and cavity 2. In addition, a pressure gauge 14 and a thermometer 15 are connected to cavity 2 to detect pressure and temperature inside cavity 2. Cavity 2 is preferably kept at a vacuum degree of 0.5 kPa to 80 kPa in a low vacuum range (between 100 Pa of absolute pressure and atmospheric pressure).

Vessel 4 preserves dinitrogen tetraoxide liquid in the condition of point O2 of temperature: 15 degrees C. and pressure: 200 kPa; after dinitrogen tetraoxide liquid in vessel 4 has been supplied into cavity 2 at reduced or negative pressure, the condition changes from O2 in the downward decompressed direction A in FIG. 2 across the saturated vapor pressure curve; and at least some amount of dinitrogen tetraoxide may be turned into gas in cavity 2, resulting in the increase in percentage of nitrogen dioxide according to the equilibrium equation. In other words, dinitrogen tetraoxide liquid instantly evaporates in cavity 2 at negative pressure into nitrogen dioxide gas that instantaneously spreads throughout whole cavity 2, and moreover, nitrogen dioxide gas promptly gets into touch with and touches the whole intricately formed surfaces of medical instruments 1 to oxidize or nitrate extraneous matters or microorganisms on surfaces of medical instruments 1 for their instantaneous and reliable sterilization. When nitrogen dioxide is used to sterilize a content of cavity 2 maintained at a given pressure and at a given temperature, sterilization time may preferably be selected in a range between tens of seconds and tens of minutes as the sterilization time is basically subject to volume of cavity 2 and size, number and shape of internal medical instruments 1. In this case, feed pipe 12 may provide a heater 21 arranged adjacent to or within feed pipe 12 to heat the sterilant flowing through feed pipe 12 to assist it to evaporate while controlling the increment percentage of generated nitrogen dioxide in cavity 2. Heater 21 can be used to heat dinitrogen tetraoxide to a preferable temperature in a range of 30 to 50 degrees C. or 50 to 80 degrees C. Heater 21 may comprise a housing for defining a medium space through which heating medium passes around feed pipe 12 to perform heat exchange between sterilant in feed pipe 12 and heating medium such as steam or heating fluid in medium space. To this end, feed pipe 12 may have a large outer surface into a spiral, coiled, finned or corrugated shape. Other type of heating elements may be used such as Nichrome wires or a film or membrane heater provided on a part of outer surfaces of feed pipe 12. Otherwise, feed pipe 12 may have an electrical insulator as a part thereof to be a heating element that can emit heat when electric current flows between opposite ends of the insulator. Also, a pair of electrodes are disposed in feed pipe 12 to apply electric voltage between different points in sterilant liquid to induce Joule heat.

The present invention should not be viewed to cover the embodiment that only introduces dinitrogen tetraoxide alone into cavity 2, and the invention also contemplates the addition of one or more attenuants from a gas source 17 to sterilant through feed pipe 12 before, after or at the same time of introduction or supply of sterilant into cavity 2. Addition of diluent or attenuant gas or gases to sterilant through feed pipe 12 can provide a variety of advantages, and in detail, firstly, attenuant gas serves to dilute in cavity 2 nitrogen dioxide derived from dinitrogen tetraoxide, this means that necessary sterilization may be attained with lesser amount of dinitrogen tetraoxide while saving substantially used amount of dinitrogen tetraoxide for inexpensive sterilization. Secondly, operators can easily and optionally adjust nitrogen dioxide to an appropriate concentration with added attenuant gas in terms of size, quantity, configuration and material of the objects or medical instruments 1 contained in cavity 2, and an appropriate attenuant gas may be selected from one or more groups consisting of water vapor, oxygen, nitrogen, air and inert gas. The thinner gas serves to thin nitrogen dioxide-base nitrogen oxide in cavity 2; a water vapor component in thinner gas works to adjust moisture content in cavity 2; and an oxygen component becomes an oxidizer of a bactericidal action. The sterilizer may preferably contain nitrogen dioxide of the concentration for example between 0.01 and 80 volume % of the total sterilant gas inclusive of thinner gas.

To collect used nitrogen oxide gas in cavity 2 after sterilization, depressure valve 24 is closed to operate vacuum pump 3 and thereby gas in cavity 2 is discharged from outlet 6 through a cooler 22 in suction pipe 11 from cavity 2. Cooler 22 cools down or condenses gases from cavity 2 to a temperature equal to or less than well-liquefied or devolatilized temperature of nitrogen oxide gas (in the cooling direction shown by Arrow B in FIG. 2) so that dinitrogen tetraoxide-base nitrogen oxide liquid may be withdrawn through a drain 23 of cooler 22. To efficiently recover dinitrogen tetraoxide liquid, nitrogen oxide is required to be cooled at a temperature of 4 to 10 degrees C. In this case, while operating vacuum pump 3 to discharge gas in cavity 2 from outlet 6 toward cooler 22, nitrogen gas may be introduced from gas supply 17 into cavity 2 or air may be introduced into cavity 2 through a restoration filter 18 and a pressure-recovery valve 7 as a pressure controller to clean inside of cavity 2. This cleaning operation is repeated as necessary to completely remove nitrogen oxide remaining in cavity 2 and adhering on medical instruments 1. Restoration filter 18 is used to collect all airborne bacteria to provide sterile air into cavity 2.

After restoring dinitrogen tetraoxide liquid from drain 23, full amount of air is brought through pressure-recovery valve 7 into cavity 2 to return it to atmospheric pressure to open a door of sterilization chamber 10 and to remove medical instruments 1 from cavity 2. In this case, it is noted that medical instruments 1 removed from cavity 2 can immediately be reused because all bacteria and viruses airborne and adhering to medical instruments 1 have been completely annihilated and destroyed with nitrogen oxide gas during sterilization, while all sterilant components are fully removed by discharging gas in cavity 2 for ensurement of high atoxic safety to human body.

Figure 3:
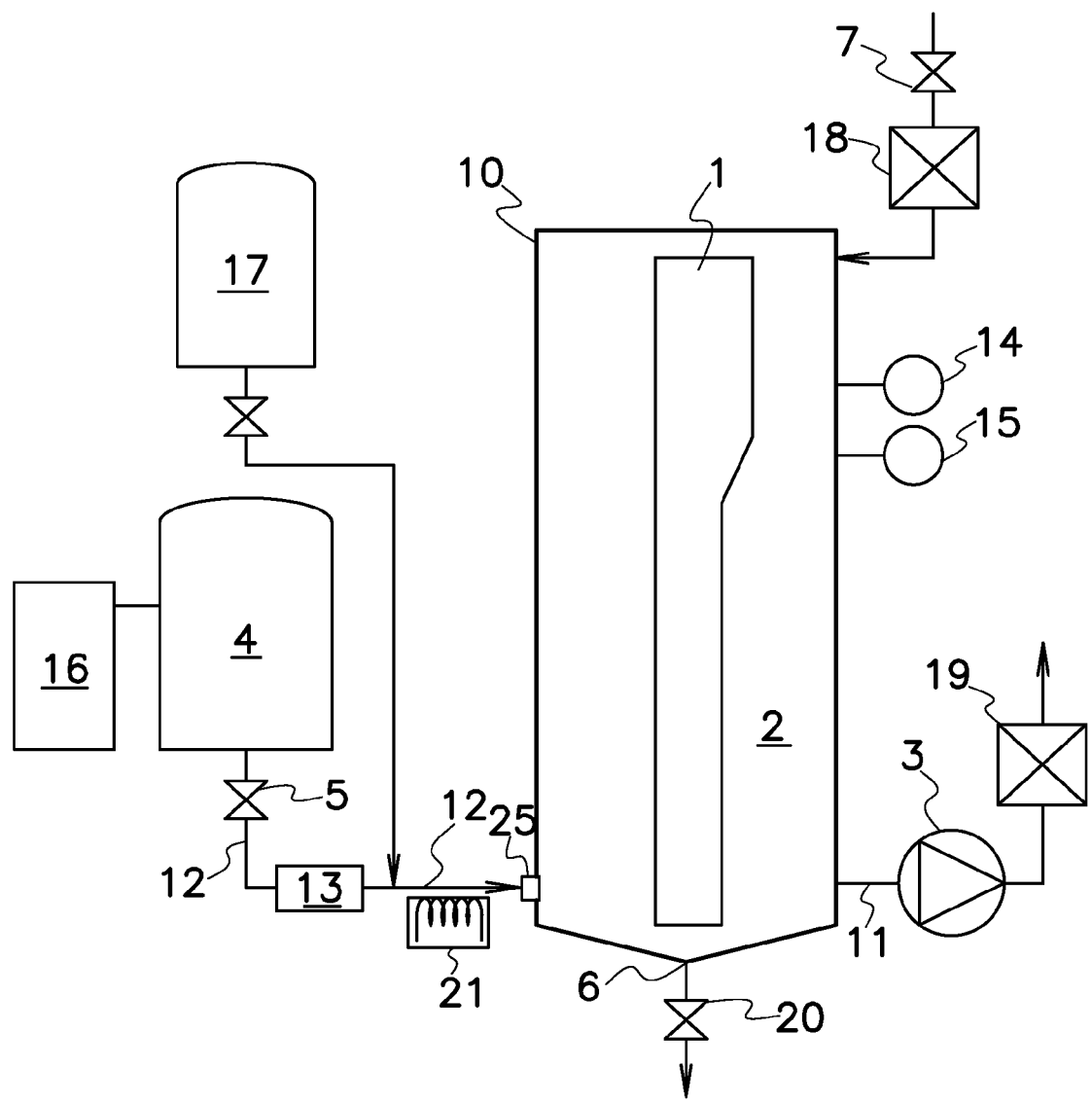
FIG. 3 A schematic diagram showing a second embodiment of the sterilization apparatus according to the present invention.

Whereas the foregoing embodiment demonstrates an example of an recovery by suction and cooling of nitrogen oxide gas from cavity 2, a second embodiment will be described hereinafter in connection with FIG. 3 on recovery of nitrogen oxide liquid by condensation under pressure in cavity 2.

After sterilization, air or inert gas is taken into cavity 2 under negative pressure through pressure-recovery valve 7 of pressure controller and restoration filter 18 to increase and restore inner pressure in cavity 2 to atmospheric pressure going up across the saturated vapor pressure curve (in the pressurizing direction shown by Arrow C in FIG. 2) to condense nitrogen oxide gas into liquid. Here, it comes to a next condition that nitrogen oxide gas attaching and adhering to whole surfaces of medical instruments 1 is condensed under an atmospheric pressure into nitrogen oxide liquid that drops on a bottom of cavity 2. As air in cavity 2 still remains gaseous while condensing nitrogen oxide, the apparatus can efficiently extract nitrogen oxide liquid from air in cavity 2 for a short recovery time. When nitrogen oxide is condensed into liquid at a temperature: 20 degrees C. at an atmospheric pressure (101.3 kPa), it comprises about 25% nitrogen dioxide and about 75% dinitrogen tetraoxide of the total nitrogen oxide under the above-mentioned chemical equilibrium equation.

Next, drainage valve 20 is opened to withdraw dinitrogen tetraoxide-base nitrogen oxide liquid through outlet 6 at the bottom of sterilization chamber 10 outside cavity 2. Thus, dinitrogen tetraoxide can be recovered with high efficiency from outlet 6 without need of any additional device such as a ventilator for removing or exhausting nitrogen oxide gas. Other than air, nitrogen gas may be introduced to pressurize inside of cavity 2. Sterilization chamber 10 may provide a centrifugal separator for mechanically and compulsorily separating and completely removing nitrogen oxide liquid remaining around medical instruments 1 in cavity 2.

The second embodiment illustrates the condensation of nitrogen oxide in cavity 2 under pressure, but alternatively, a temperature controller not shown may be used to condense nitrogen oxide by reduction in temperature in cavity 2.

Figure 4:
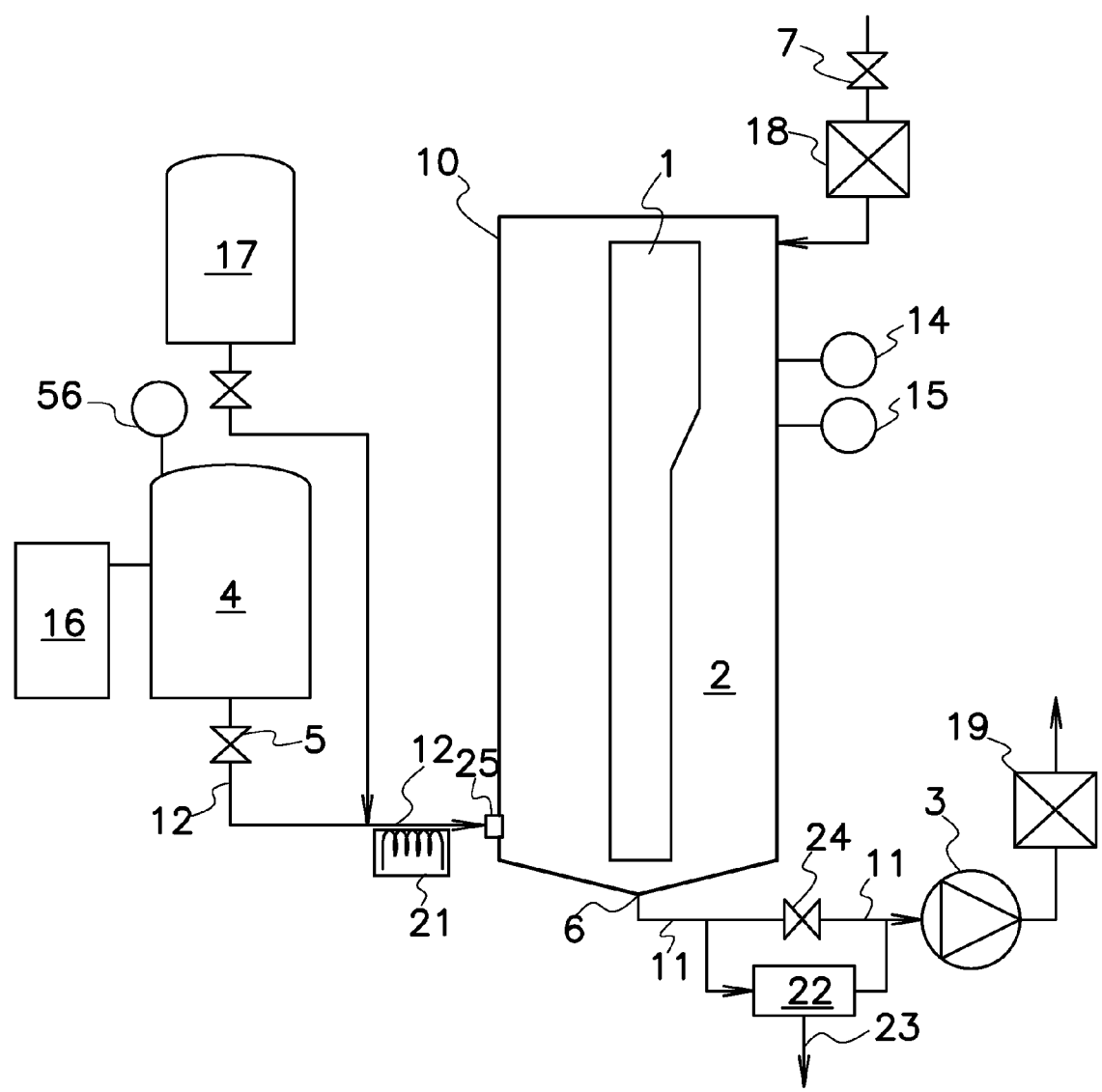
FIG. 4 A schematic diagram showing a third embodiment of the sterilization apparatus according to the present invention.

Unlike the first and second embodiments, a third embodiment shown in FIG. 4 may comprise a pressure gauge 56 at the upstream of control valve 5 without flowmeter 13. Pressure gauge 56 indicates a pressure value in vessel 4 to determine flow rate per unit time of nitrogen oxide liquid together with an inner diameter value of feed pipe 12, and therefore, release time of control valve 5 may be controlled depending on pressure value on pressure gauge 56 to simply and precisely adjust feed rate of nitrogen oxide liquid to cavity 2.

Figure 5:
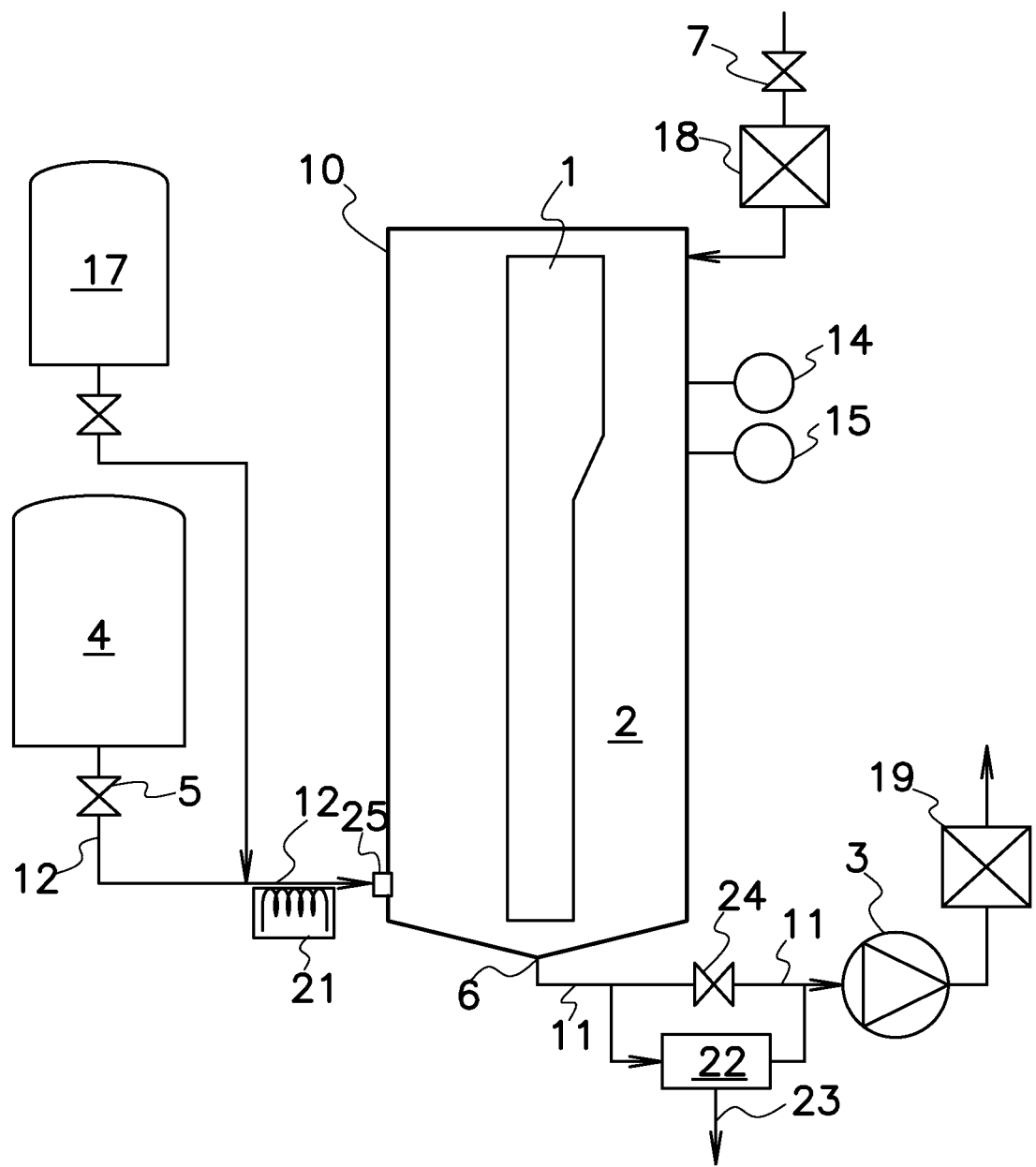
FIG. 5 A schematic diagram showing the forth embodiment of the sterilization apparatus according to the present invention.

A fourth embodiment shown in FIG. 5 illustrates a sterilization apparatus that comprises a vessel 4 filled under pressure with a predetermined necessary amount of nitrogen oxide liquid. To sterilize objects 1 in cavity 2 according to this embodiment, a full amount of nitrogen oxide liquid is supplied through opened control valve 5 from vessel 4 connected via feed pipe 12 into cavity 2. Thus, a specific amount of nitrogen oxide liquid can be constantly supplied into cavity 2 for assured sterilization of objects 1 without any flow rate control. Vessel 4 may include a small bomb or tank. This embodiment may dispense with any flowmeter 13, compressor 16 and pressure gauge 56 provided upstream of control valve 5 in FIGS. 1, 3 and 4.

In lieu of control valve 5 provided between vessel 4 and heater 21 in the first to fourth embodiments, control valve 5 may be connected between heater 21 and cavity 2. Also, with or without control valve 5, it is possible to use spray device 25 provided at the inlet of cavity 2 as a valve.

With reference to FIGS. 6 to 12, further embodiments of the present invention will be described hereinafter relevant to the sterilization apparatus and method that are applied to sterilizing operations for clean rooms 50 and medical instruments 1 as unsterilized objects in chamber 50.

Applied to sterilizing operations of clean rooms 50 is the sterilization apparatus 40 of the present invention that comprises: a vessel 4 for storing nitrogen oxide liquid, a spray device or an ejector 32 for spraying nitrogen oxide liquid with its gasification or evaporation into a space area (space to be sterilized) 2' in clean room 50 at a substantially atmospheric pressure, and a metering pump 34, 34' for suctioning a predetermined amount of nitrogen oxide liquid from an outlet port 37 of vessel 4 to metering pump 34, 34' and supplying the liquid toward spray device 32. Spray device 32 may be a nozzle or a valve.

The term "at a substantially atmospheric pressure" herein means a pressure value in range of 90 kPa to 110 kPa. Nitrogen oxide liquid in vessel 4 is one or more kinds selected from the groups of dinitrogen trioxide, dinitrogen pentaoxide and more preferable dinitrogen tetraoxide. Dinitrogen tetraoxide liquid alone can advantageously turn into a highly-dispersible sterilant gas by a simple pressure control operation without admixing other substances thereto.

Dinitrogen tetraoxide having its boiling point 21 degrees C. is easy to handle for preservation and conveyance at a temperature below the boiling point free from any high-pressure filling and any pressure-resistant vessel. The above-mentioned chemical equilibrium equation is given between dinitrogen tetraoxide and nitrogen dioxide ($NO_2$).

Metering pump 34, 34' is selected from diaphragm, plunger and tube pumps, more preferably, piston pumps. Metering pump (piston pump 34) is used to evacuate a predetermined amount of nitrogen oxide liquid from vessel 4 through an outlet port 37 for precise measurement and deliver it under pressure toward spray device 32. Nitrogen oxide liquid is conveyed through tubing 38 toward cavity 2, and the absolute pressure value in tubing 38 just before space area or cavity 2', 2" is of 110 kPa to 50000 kPa. The pressure value of less than 110 kPa weakens a pumping force for conveying nitrogen oxide liquid and reduces a spraying force of nitrogen oxide liquid within an asepsis-targeted space area 2', resulting in insufficient evaporation and dispersion, delayed diffusion and inconsistent concentration distribution of nitrogen oxide liquid within space area 2'. Adversely, the pressure value of more than 50000 kPa would require expensive high-pressure spray device 32 and a larger-sized metering pump 34, 34'.

Spray device 32 may comprise a jet orifice 32a with its adjustable aperture (spray area) for injecting, spraying or atomizing nitrogen oxide liquid into clean room 50 at a substantially atmospheric pressure. This embodiment may also utilize a commercially available spray device 32 with fixed or unadjustable jet orifice 32*a*. Spray device 32 can advantageously inject, spray or atomize nitrogen oxide liquid of the uniform concentration within a whole of clean room 50 to certainly sterilize airborne microorganisms and bacteria in clean room 50 and also similar microbes attaching and adhering to walls and floors of the room 50.

The embodiment shown in FIG. 6 incorporates a three-way valve 35 that comprises a first input port 35*a* connected to vessel 4, a second I/O port 35*b* connected to metering pump 34, 34', and a third output port 35*c* connected to spray device 32. Three-way valve 35 of its antimicrobial simple inner structure includes, but not particularly limited to, a ball or spherical valve element 45 and a right-angled flow path 46 formed in valve element 45. Three-way valve (ball valve) 35 may be shifted as required between a charge position for connecting metering pump 34, 34' to vessel 4 and simultaneously disconnecting metering pump 34, 34' from spray device 32 and a discharge position for disconnecting metering pump 34, 34' from vessel 4 and simultaneously connecting metering pump 34, 34' to spray device 32. Metering pump 34, 34' may be selected from for example, plunger, diaphragm and rotary tube pumps.

A tubing heater 36 is provided between metering pump 34, 34' and spray device 32 to heat nitrogen oxide liquid before splashing from spray device 32. Referring to FIG. 7, nitrogen oxide liquid preserved in vessel 4 (at a point O2) is pressure-applied by metering pump 34, 34' in the pressurized direction (Arrow A), and then heated by heater 36 in the heated direction (Arrow B) to release nitrogen oxide liquid into clean room 50 at an approximately atmospheric pressure in the depressurized direction (Arrow C), and thereby, nitrogen oxide liquid goes down across the saturated steam pressure curve of dinitrogen tetroxide (nitrogen dioxide) in FIG. 7 that rapidly turns into nitrogen oxide gas in clean room 50 for efficient filling with nitrogen oxide gas.

Heater 36 comprises an outer cell 36*b* for defining a medium room and conduits 36*a* arranged within medium room for feeding nitrogen oxide liquid wherein conduits 36*a* are formed into a spiral, finned, coiled or corrugated shape to have their expanded outer surfaces in thermally exchangeable contact to heating medium such as water steam or heating fluid in medium room to heat nitrogen oxide liquid through conduits 36*a*. Spiral conduits 36*a* has their larger outer surfaces for thermal contact of nitrogen oxide liquid to heating medium for improved efficiency in heat exchange. Other type of heaters 36 may be used as a heating element such as Nichrome wires or film heaters attached to outer surfaces of conduits 36*a*. Otherwise, conduits 36*a* may have an electrical insulator as a part thereof to be a heating element that can emit heat when electric current flows between opposite ends of the insulator. Also, a pair of electrodes may be disposed in conduits 36 to apply electric voltage and generate electric current between different points in sterilant liquid to induce Joule heat. Heater 36 is used to heat nitrogen oxide liquid before spray device 32 at a temperature in a range of 25 to 150 degrees C.

With reference to FIGS. 6 and 7, embodiments of the present invention will be described hereinafter as to usage of nitrogen oxide (dinitrogen tetraoxide) for sterilization of a clean room.

Initially, dinitrogen tetroxide liquid is stored in vessel 4. Although dinitrogen tetraoxide liquid has strongly oxidizing ability, it can be safely preserved in vessel 4 at a temperature less than 21 degrees C. (of the boiling point) at an increased absolute pressure in the order of 200 kPa (approximately 2 atm) (from point O1 to O2 in FIG. 7). Here, asepsis-targeted clean room 50 is hermetically kept for prevention of nitrogen oxide from leaking outside.

Now, three-way valve 35 is in the charge position that connects metering pump 34, 34' to vessel 4 through first and second ports 35*a*, 35*b* while simultaneously disconnecting metering pump 34, 34' from spray device 32. Then, metering pump 34 is operated to take a predetermined amount of nitrogen oxide liquid from vessel 4 through bottom port 37 in a variable volume (a cylinder) 34*a* of metering pump 34 for temporary storage while exactly and rapidly measuring the suction quantity of the liquid.

Then, three-way valve 35 is shifted to turn valve element 45 around to the discharge position that connects second and third ports 35*b*, 35*c* to communicate variable volume 34*a* of metering pump 34, 34' with spray device 32 while simultaneously disconnecting variable volume 34*a* from vessel 4, and subsequently, metering pump 34, 34' is further operated to eject dinitrogen tetroxide liquid from variable volume 34*a* of metering pump 34, 34' toward spray device 32 in the pressurized direction (Arrow A in FIG. 7) through heater 36 to heat the liquid to an elevated temperature (Arrow B in FIG. 7).

Thus, metering pump 34, 34' works to forward a predetermined amount of nitrogen oxide liquid to spray device 32 and further to allow the liquid to spout through a jet orifice 32a of spray device 32 by injecting and spraying the liquid into gas in depressurized space area 2' of clean room 50 (Arrow C in FIG. 7). At the moment, pressurized and heated dinitrogen tetroxide liquid immediately evaporates into gas dispersing into whole area of clean room 50 kept at the substantially atmospheric pressure. Dispersed nitrogen oxide indicates a mixed gas of dinitrogen tetroxide and nitrogen dioxide.

In this embodiment, space area 2' is constantly filled with nitrogen oxide gas of the predetermined concentration since metering pump 34, 34' serves to supply an exactly given amount of nitrogen oxide to space area 2' of clean room 50. Dispersed nitrogen oxide gas remains in space area 2' during sterilization to completely deaden microorganisms and bacteria adhering or attaching onto walls and floor surfaces in clean room 50 so sterilization time is decided depending on volume and content of clean room 50 between several minutes and several hours.

Figure 6:
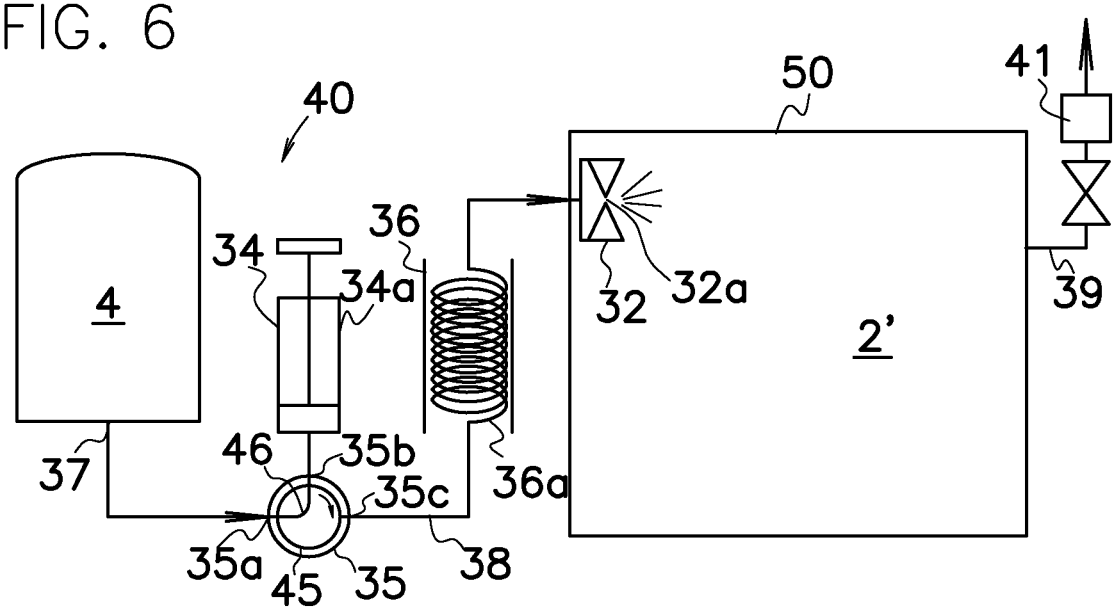
FIG. 6 A schematic diagram showing a fifth embodiment of the sterilization apparatus according to the present invention.
Figure 7:
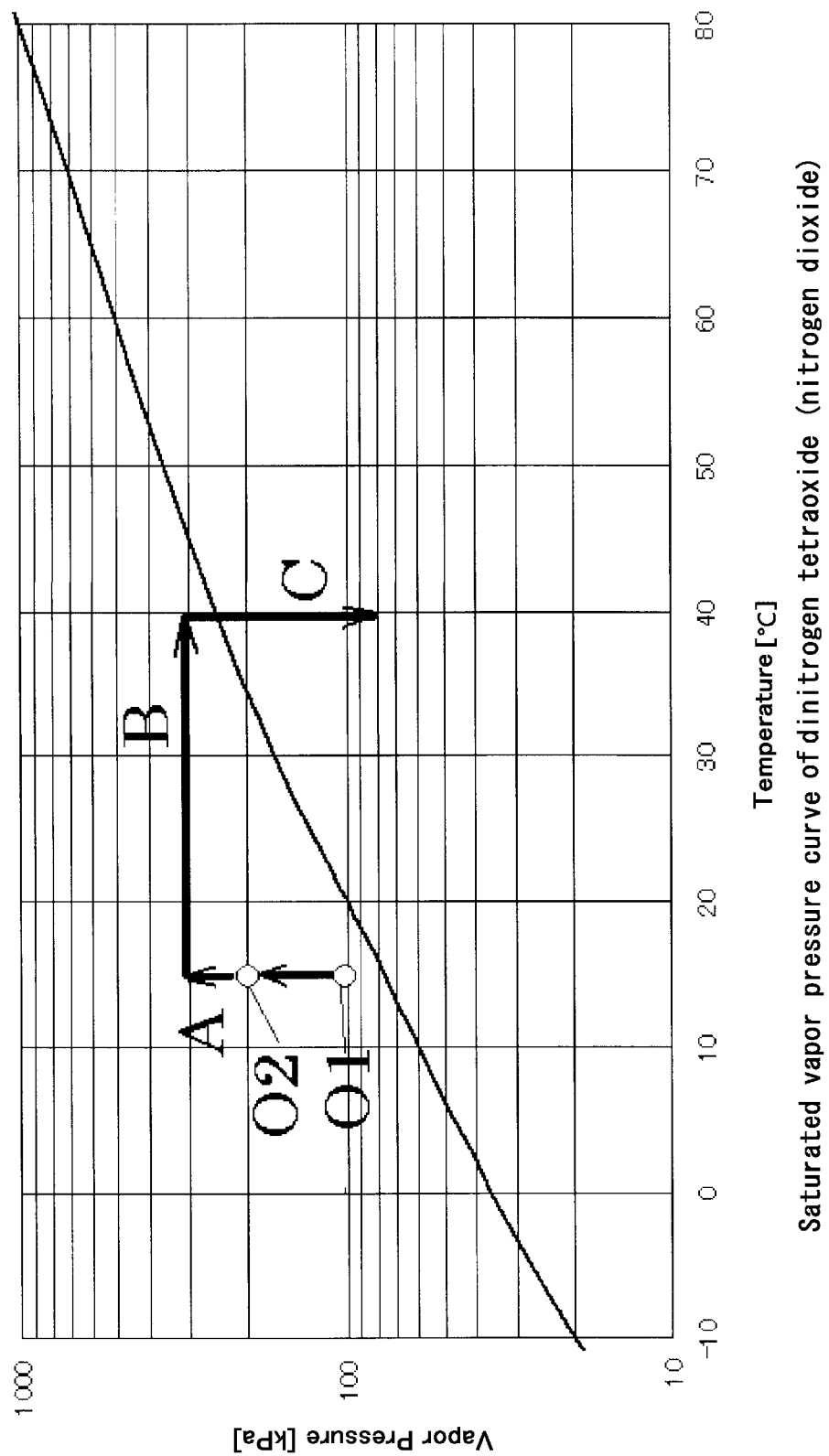
FIG. 7 A graph showing a saturated vapor pressure curve of dinitrogen tetraoxide (nitrogen dioxide) with temperature and vapor pressure variations.

The embodiment shown in FIG. 6 contemplates to return residual nitrogen oxide liquid in conduit 38 between three-way valve 35 and spray device 32 to vessel 4 after sterilization. To this end, three-way valve 35 is shifted to turn valve element 45 around to the discharge position that connects metering pump 34, 34' and spray device 32, and metering pump 34, 34' is operated to return nitrogen oxide in conduit 38 to variable volume 34a of metering pump 34, 34'. Then, three-way valve 35 is shifted to rotate valve element 45 to the charge position that connects metering pump 34, 34' to vessel 4 through first and second ports 35a, 35b to return nitrogen oxide in variable volume 34a to vessel 4. Meanwhile, introduced into clean room 50 is washing gas (nitrogen gas or air) from an intake not shown of clean room to ventilate and remove nitrogen oxide from clean room 50. Nitrogen oxide can be completely removed by a removal filter 41 connected to clean room 50 through an exhaust pipe 39 while continuously supplying washing gas into clean room 50. This embodiment illustrates a sterilization of clean room 50, however, it would be apparent to those skilled in the art that the embodiment may also apply to the sterilization for clean booths, isolators, sickrooms and operating rooms.

Figure 8:
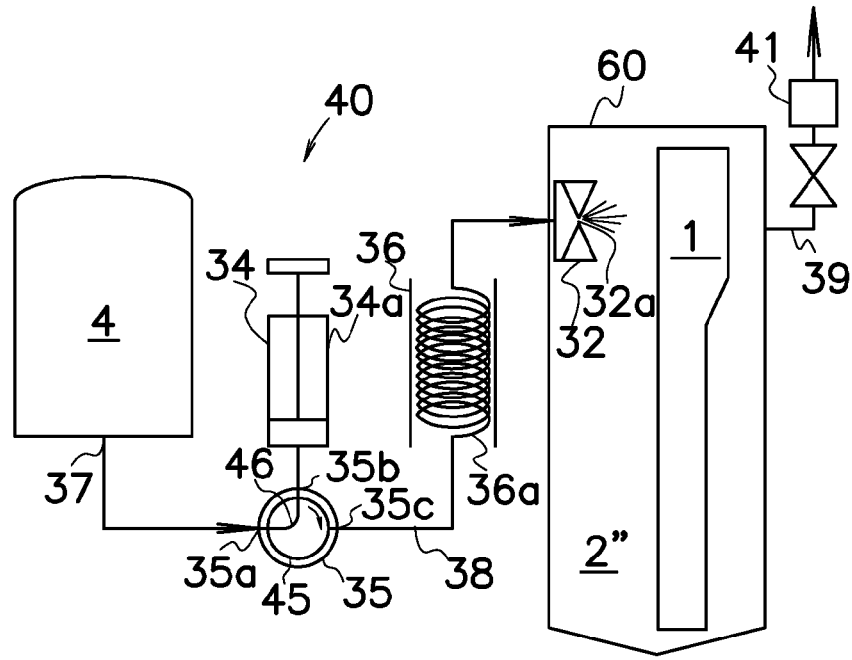
FIG. 8 A schematic diagram showing a sixth embodiment of the sterilization apparatus according to the present invention.

FIG. 8 illustrates a sixth embodiment of the present invention referred to a sterilization apparatus and method for medical instruments 1 in a sterilization chamber 60. Same reference symbols as those shown in the fifth embodiment are applied to similar portions in FIG. 8, without explanation thereon. Only differences from the fifth embodiment will be described hereinafter.

Asepsis-targeted medical instruments 1 or containers are placed in a cavity 2" of sterilization chamber 60. The present invention is applicable to sterilization of medical instruments 1 made of any and all metallic, plastic and rubber materials resistible against deterioration by nitrogen oxide. Medical instruments 1 may include surgical instruments such as scalpels, forceps, scissors and tweezers; diagnostic instruments such as flexible or rigid endoscopes, clinical thermometers, stethoscopes, funduscopes and aural speculums; therapeutic instruments such as catheters, injection syringes and medical tubing; and implantable medical instruments such as pacemakers, implantable aggregate and surgical pins. Medical containers may include such as plastic and glass containers, vials, spray cans, aluminum tubes, rubber plugs, elastomeric products and injection needles. The present invention is also applicable to preliminary, last-minute or emergent sterilization before use of medical instruments 1. A door not shown is attached to hermetically-closed cavity 2" into the sealed condition covering inner medical instruments 1.

Cavity 2" of sterilization chamber 60 is kept at an approximately atmospheric pressure. In a similar manner as in the fifth embodiment, a sterilization apparatus 40 supplies nitrogen oxide liquid to inject it via a spray device 32 into cavity 2" of sterilization chamber 60. Injected nitrogen oxide liquid immediately gasifies and spreads in cavity 2" for sterilization of medical instruments 1. As nitrogen oxide gas immediately spreads and diffuses in cavity 2" approaching whole surfaces of medical instruments 1 to rapidly and completely sterilize all surfaces of intricate details of medical instruments 1. According to the embodiment, metering pump 34, 34' can be used to exactly control an amount of nitrogen oxide liquid to sterilization chamber 60 so that operators can decide an appropriate amount of nitrogen oxide liquid depending on quantity, size, material and contaminated level of medical instruments 1.

Figure 9:
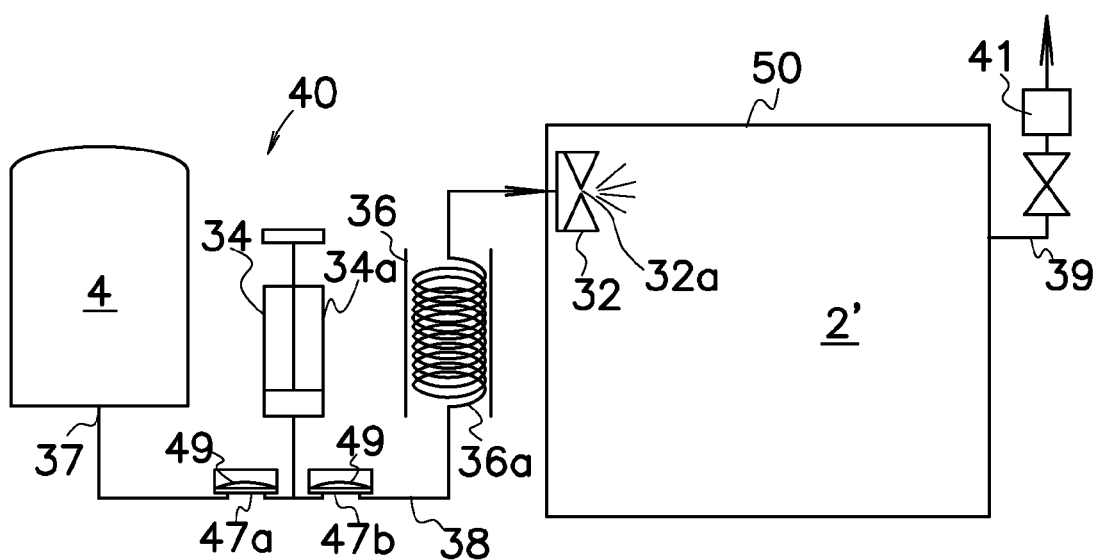
FIG. 9 A schematic diagram showing a seventh embodiment of the sterilization apparatus according to the present invention provided with a two-way valve.

In lieu of three-way valve 35 that switches between vessel 4 and metering pump 34, 34' and between metering pump 34, 34' and spray device 32 in the fifth and sixth embodiments, a pair of two-way valve 47a, 47b may be used in a seventh embodiment in FIG. 9. Two-way valve comprises a suction valve 47a between vessel 4 and metering pump 34, 34' and a delivery valve 47b between metering pump 34, 34' and spray device 32. A charge position is established by opening suction valve 47a and at the same time closing delivery valve 47b to take nitrogen oxide liquid from vessel 4 in metering pump 34, 34'. Whereas a discharge position is established by closing suction valve 47a and at the same time opening delivery valve 47b to supply nitrogen oxide liquid from metering pump 34, 34' to spray device 32. This embodiment may utilize diaphragm valves with gating diaphragms 49 for both suction and delivery valves 47a, 47b, but not limited thereto. Alternate opening and closing operations of valves 47a, 47b allows for gating between the charge and discharge positions.

Figure 10:
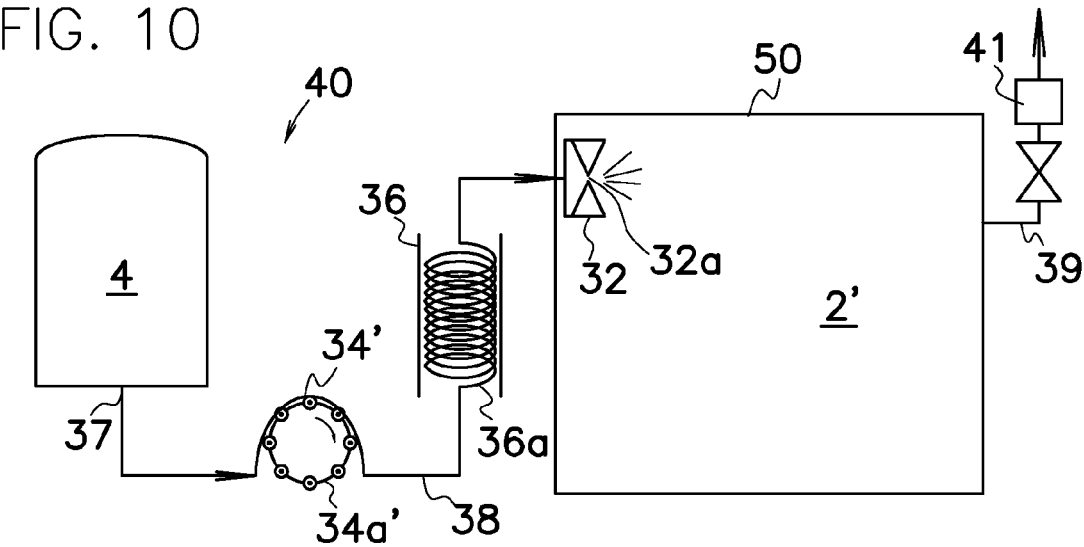
FIG. 10 A schematic diagram showing an eight embodiment of the sterilization apparatus according to the present invention provided with a tube pump in place of the two-way valve in FIG. 9.

Whereas the fifth to seventh embodiments use piston pump 34 as metering pomp for temporarily storing and measuring nitrogen oxide liquid, an eighth embodiment shown in FIG. 10 utilizes a tube pump 34' to directly forward nitrogen oxide liquid from vessel 4 to spray device 32. Tube pump 34' has a rotator 34a' that rotates to generate discharge flow rate in proportion to its rotation speed to achieve a given conveyance amount of nitrogen oxide liquid.

Figure 11:
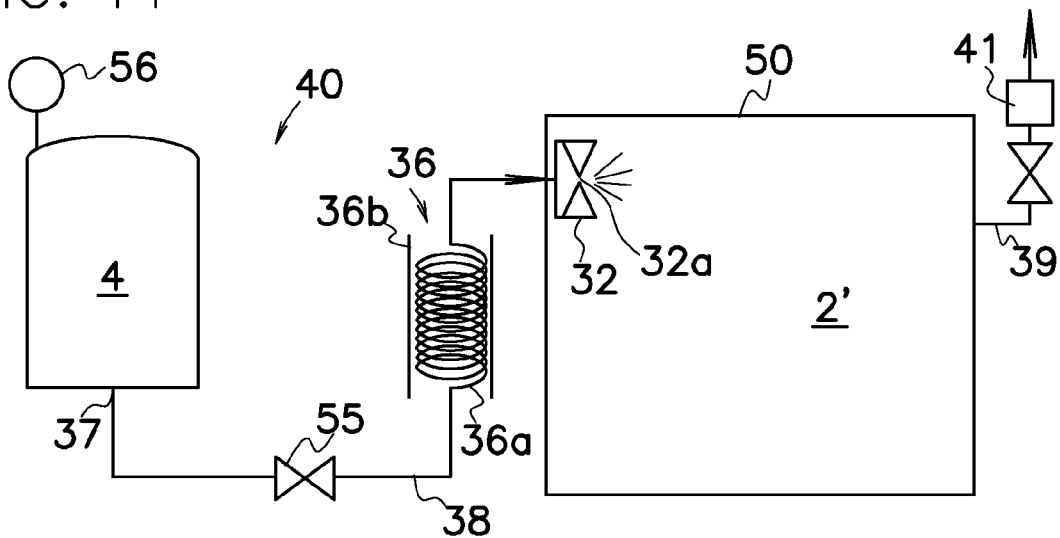
FIG. 11 A schematic diagram showing a ninth embodiment of the sterilization apparatus according to the present invention provided with a control valve and a pressure gauge.

A ninth embodiment shown in FIG. 11 comprises a control valve 55 on the way through conduit 38 between vessel 4 and space area 2', and a pressure gauge 56 connected to an upstream of control valve 55 with piston pump 34, tube pump 34', three-way valve 35, suction valve 47a and delivery valve 47b all removed. As a pressure value indicated by pressure gauge 56 provides flow rate per unit time of nitrogen oxide liquid with an inner diameter size of conduit 38, feed rate of nitrogen oxide liquid to space area 2' can simply and precisely be adjusted under control of switching time of control valve 55 depending on pressure value on pressure gauge 56.

Figure 12:
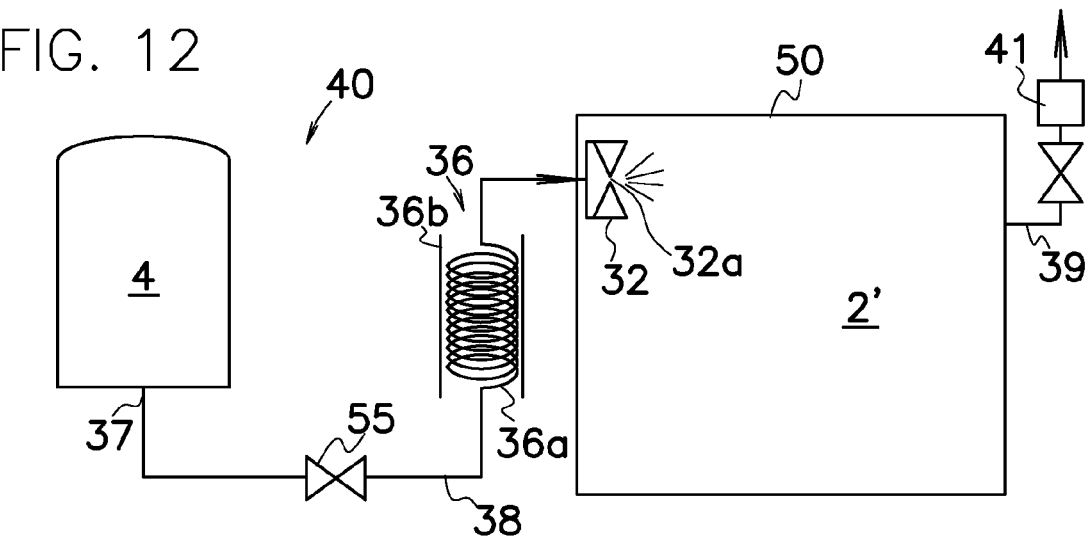
FIG. 12 A schematic diagram showing a tenth embodiment of the sterilization apparatus according to the present invention provided with a control valve without a pressure gauge.

A tenth embodiment shown in FIG. 12 comprises a sterilization apparatus provided with a vessel 4 previously filled under pressure with only a required amount of nitrogen oxide liquid. To sterilize space area 2' in the tenth embodiment, pressure in vessel 4 allows for a full amount supply of nitrogen oxide liquid to space area 2' through opened control valve 55 from vessel 4 connected via conduit 38. Thus, in the absence of any flow control, the sterilization apparatus can constantly provide a specific amount of nitrogen oxide liquid for complete sterilization of space area 2'. Vessel 4 may be a small bomb or tank. Also, this embodiment may need none of piston pump 34, tube pump 34', three-way valve 35, suction valve 47a and delivery valve 47b.

Provided between vessel 4 and heater 36 in the fifth to tenth embodiments, is control valve 55 that may instead be connected between heater 36 and space area 2'. Also, with or without control valve 55, a valve of any type may be used in exchange for spray device 32 mounted at the inlet of space area 2'.

EXAMPLE 1

A few qualification tests were carried out to find a performance and effects of annihilating microorganisms according to the sterilization method and apparatus of the present invention. The following indicates the test results:
Sterilization Test 1

An SCBI (Self-Contained Biological Indicator) was put in cavity 2 of approximately 8 liters (20 cm×20 cm×20 cm) in vacuum chamber 10. SCBI was a sterilization test kit that comprised a filter paper on which microorganism spores were attached, a glass capsule into which culture solution was put, a small test tube into which the filter paper and glass capsule were put, and an air-permeable filter for sealing the small test tube. SCBI was put in cavity 2 that was pressure-reduced up to 5 kPa to introduce into cavity 2 dinitrogen tetroxide ($N_2O_4$) liquid at a higher pressure than atmospheric pressure through spray device 25 that vaporized the liquid in cavity 2. Immediately after gasification of dinitrogen tetroxide, pressure-recovery valve 7 was opened to take clean air into cavity 2 keeping dinitrogen tetroxide at a concentration of 8,500 ppm (16.54 mg/L) for 20 minutes sterilization.

After the sterilization, pressure was reduced from inside of small SCBI test tube to remove dinitrogen tetroxide, and vacuum chamber 10 was opened to take out SCBI from cavity 2. Glass capsule was broken within a small SCBI test tube to remove the filter paper that was then dipped in a culture solution to culture sterilized SCBI in an incubator at a temperature of 58 degrees C. for approximately 24 hours (sterilized SCBI). Meanwhile, another unsterilized SCBI was left in an atmosphere for 20 minutes, and in a similar manner, the SCBI was cultured in an incubator at a temperature of 58 degrees C. for approximately 24 hours (unsterilized SCBI).
Test Result 1

No change was found in cultivation of sterilized SCBI according to the present invention that indicated no multiplication of microorganisms that could sufficiently and completely be sterilized and annihilated. In contrast, unsterilized SCBI indicated a color change that evidenced the multiplication of unsterilized microorganisms.

EXAMPLE 2

A further example is described hereinafter about sterilization tests according to the method and apparatus of the present invention.
Sterilization Test 2

Another SCBI was put in unsterilized space area or cavity 2', 2" of approximately 8 liters (20 cm×20 cm×20 cm) in vacuum chamber 10. A similar SCBI was used as that in Example 1. Metering pump 34, 34' was operated to supply dinitrogen tetroxide ($N_2O_4$) liquid to unsterilized space area 2', 2" under a pressure higher than an atomospheric pressure, and spray device 32 was provided to vaporize the liquid into cavity 2', 2" in which SCBI was put. Space area 2' 2" was kept at a dinitrogen tetroxide concentration: 18,500 ppm (36.28 mg/L) for 20 minutes sterilization.

After sterilization, SCBI was taken out of space area 2' 2" and then dinitrogen tetroxide was removed under a reduced pressure from inside of small test tube of SCBI. Then, glass capsule was broken within a small SCBI test tube to remove the filter paper that was then dipped in a culture solution to culture sterilized SCBI in an incubator at a temperature of 58 degrees C. for approximately 24 hours (sterilized SCBI). Meanwhile, another unsterilized SCBI was left at an atmosphere for 20 minutes, and in a similar manner, the SCBI was cultured in an incubator at a temperature of 58 degrees C. for approximately 24 hours (unsterilized SCBI).
Test Result 2

No change was found in cultivation of sterilized SCBI according to the present invention that indicated no multiplication of microorganisms that could sufficiently and completely be sterilized and annihilated. In contrast, unsterilized SCBI indicated a color change that evidenced the multiplication of unsterilized microorganisms.

INDUSTRIAL APPLICABILITY

The present invention is applicable to the sterilization of any objects such as medical instruments, appliances or accessories; precision apparatus, instruments or accessories; electric or electronic elements; raw materials for medicines or drugs; containers for medical purpose; food products and materials; containers for foods; and other microbially-contaminated objects. The present invention can also be applied to the sterilizations in the food and drink fields for recycling bottles and containers and in the pharmaceutical sectors. The sterilization apparatus and method according to the present invention can be further applied to the sterilizations in the precision machinery industries and electronics industries mainly semiconductors in addition to the medicine manufacture, medical care and food fields.

The invention claimed is:

1. A sterilization method with dinitrogen tetraoxide comprising the steps of:
    arranging an object in a sterilization area,
    operating a decompressor to reduce a pressure within the sterilization area maintained in the hermetically sealed condition to the decompressed or vacuum condition below the saturated vapor pressure curve of dinitrogen tetraoxide,
    supplying the dinitrogen tetraoxide liquid as a sterilant feedstock from a vessel to a spray device while preventing gasification of the dinitrogen tetraoxide liquid on the way between the vessel and spray device,
    spraying the dinitrogen tetraoxide liquid through the spray device into the sterilization area under the decompressed or vacuum condition to, at the time of the spraying, gasify at least some of the dinitrogen tetraoxide liquid within the sterilization area decompressed below the saturated vapor pressure curve, and
    sterilizing the object in the sterilization area by the oxidation or nitration of extraneous matter or microorganisms on the object with the dinitrogen tetraoxide gas.
2. The sterilization method of claim 1, wherein the object is one or more articles selected from the groups consisting of medical instruments, appliances or accessories; precision apparatus, instruments or accessories; electric or electronic elements; raw materials for medicines or drugs;

containers for medical purpose; food products and materials; containers for foods; and microbially-contaminated objects.

3. The sterilization method of claim 1, further comprising introducing diluent gas into the sterilization area before, after or at the same time of spraying the dinitrogen tetraoxide liquid into the sterilization area.

4. The sterilization method of claim 3, wherein the diluent gas is one or more gases selected from groups consisting of water vapor, oxygen gas, nitrogen gas, air and inert gas.

5. The sterilization method of claim 1, wherein the supplying of the dinitrogen tetraoxide liquid from the vessel to the spray device comprises:

opening a control valve in a feed pipe that connects between the sterilization area and a small bomb or tank as the vessel that includes a necessary amount of the dinitrogen tetraoxide liquid therein, and supplying a full amount of the dinitrogen tetraoxide liquid from the bomb or tank through the feed pipe to the spray device.

6. The sterilization method of claim 1, further comprising:

after sterilization of the object, sucking and collecting the dinitrogen tetraoxide gas through an outlet of the sterilization area to cool and condense the collected dinitrogen tetraoxide gas into liquid.

7. The sterilization method of claim 1, further comprising:

after sterilization of the object, applying the pressure on or cooling the temperature of the dinitrogen tetraoxide gas in the sterilization area across the saturated vapor pressure curve of dinitrogen tetraoxide to condense the dinitrogen tetraoxide gas into liquid within the sterilization area, collecting the condensed dinitrogen tetraoxide liquid through an outlet of the space area, and removing the object out of the sterilization area.

8. The sterilization method of claim 1, wherein the supplying of the dinitrogen tetraoxide liquid from the vessel to the spray device comprises:

heating the dinitrogen tetraoxide liquid by a heater connected between the vessel and the spray device to spray the heated dinitrogen tetraoxide.

* * * * *